United States Patent [19]

Germain et al.

[11] Patent Number: 5,319,953
[45] Date of Patent: Jun. 14, 1994

[54] FRICTION INDEX TESTER

[75] Inventors: Paul Germain, Montreal; Douglas Milne, Vancouver, both of Canada

[73] Assignee: Noranda Inc., Toronto, Canada

[21] Appl. No.: 42,204

[22] Filed: Apr. 2, 1993

[30] Foreign Application Priority Data

Apr. 7, 1992 [CA] Canada .................. 2065524

[51] Int. Cl.⁵ ............................ G01N 19/02
[52] U.S. Cl. ............................ 73/9
[58] Field of Search ..................... 73/9, 10

[56] References Cited

U.S. PATENT DOCUMENTS

| | | | |
|---|---|---|---|
| 2,690,668 | 10/1954 | Lucas | 73/9 |
| 2,955,455 | 10/1960 | Frederik | 73/9 |
| 3,187,552 | 6/1965 | Davies | 73/9 |
| 4,051,713 | 10/1977 | Bao et al. | 73/9 |
| 4,712,418 | 12/1987 | Augustin | 73/10 |
| 4,798,080 | 1/1989 | Brungraber | 73/9 |
| 4,890,477 | 1/1990 | Losev et al. | 73/9 |
| 4,909,073 | 3/1990 | Takahashi | 73/146 |

OTHER PUBLICATIONS

Rae, D. in *J. Sci. Intrum.*, 1963, 40, 438–440.
Database WPI, Section EI, Week 9022, Derwent Publications Ltd., London, GB; Class S03, AN 90-170483/22.

*Primary Examiner*—Robert Raevis
*Assistant Examiner*—Daniel S. Larkin
*Attorney, Agent, or Firm*—Keck, Mahin & Cate

[57] ABSTRACT

An apparatus for measuring the basic friction angle of a surface of given material comprises a housing adapted to be held against a surface of material to be tested, a base which can slide along the inside wall of the housing, a wheel mounted on the lower part of the base and adapted to contact the surface to be tested, a spring for applying a load on the base to force the wheel against the surface to be tested, and a torque gauge for applying a torque to the wheel, and for measuring the maximum torque required to spin the wheel on the surface to be tested at various loads applied to the base.

2 Claims, 1 Drawing Sheet

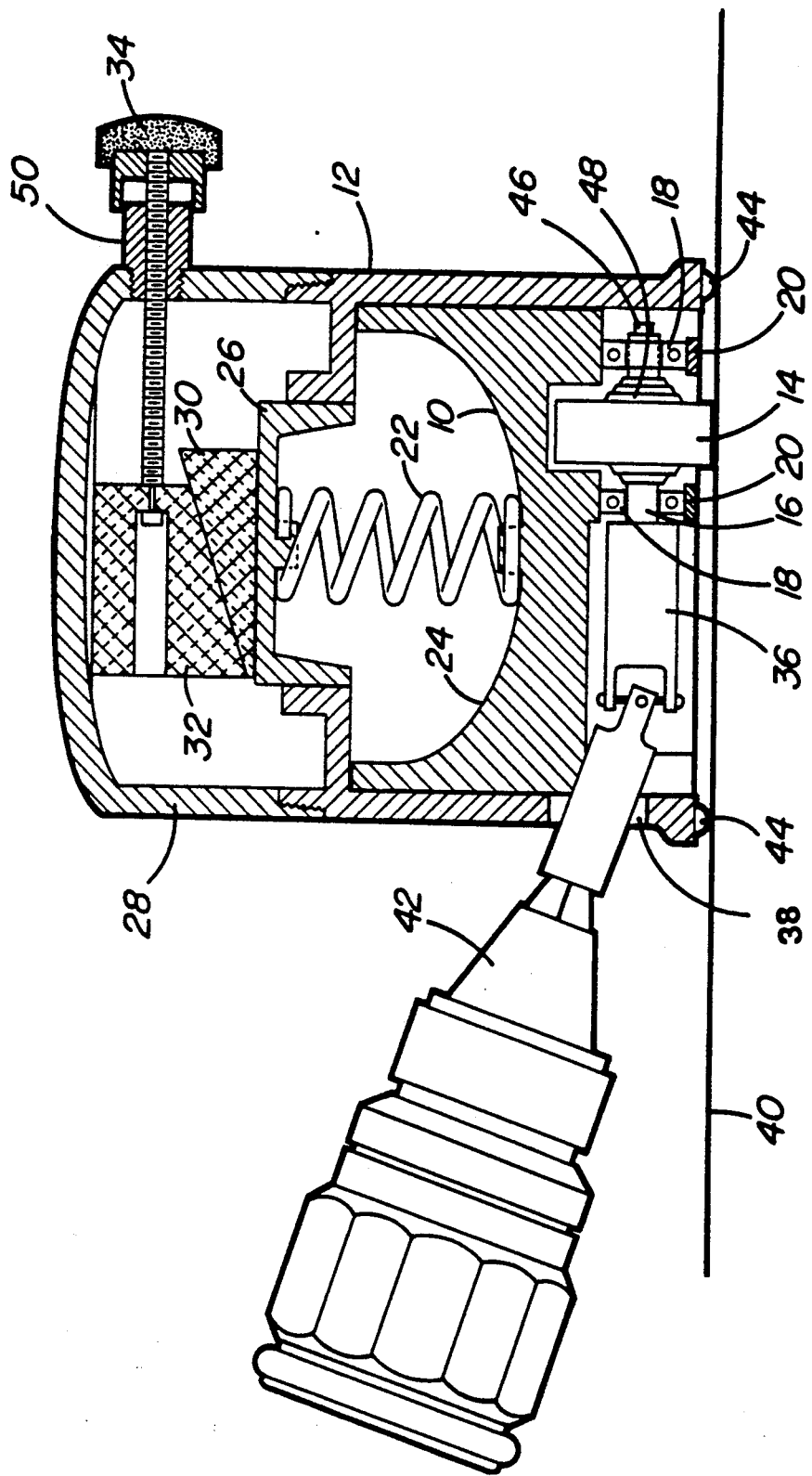

FRICTION INDEX TESTER

This invention relates to an apparatus for measuring the basic friction angle of the surface of a given material, and more particularly, to an apparatus for measuring the basic friction angle of surfaces of rock materials.

BACKGROUND OF THE INVENTION

The friction angle is the slope of the curve representing on a graph the frictional force between two bodies in contact, parallel to the surface of contact, plotted on the vertical axis, versus the force normal to the surface of contact with which the bodies are pressed against each other, plotted on the horizontal axis. Mathematically, the friction angle $\phi$ is defined as follows:

$$\phi = \tan^{-1}\left(\frac{Fc}{Fn}\right)$$

where
Fc=frictional force between the two bodies in contact
Fn=force normal to the surface of contact The friction angle of surfaces of rock materials is often used as one parameter to measure the degree of roughness and alteration of rock fracture surfaces.

Basic friction angles can be generally measured either in a laboratory or on site using a shear test apparatus. Such apparatus consists of two half portions forming a box, each portion being adapted to contain one part of a rock sample which is cut in half by means of a saw blade. Preparation of the test sample requires cutting of the rock sample in two parts, fixing each part in one half of the box, with the cut surface facing up, pouring grout mix around each half sample and waiting for the grout to set. It is thus time consuming. The test itself is performed as follows:

The upper half of the box is pressed down against the lower half with an hydraulic press thus placing the facing cut surfaces under a specific amount of normal load. The bottom part of the box is then moved back and forth horizontally with the help of a hydraulic jack and the shear force required to move the bottom part of the box is measured. The test is performed with different values of normal load.

If the saw cut surface is not perfectly planar, the lateral movement of the bottom part of the sample will shear off micro-roughnesses on the contacting surfaces of the sample and produce crushed material. The friction angle obtained during such test approximates the residual friction angle. When the rock surface is perfectly planar with no roughnesses due to geometric asperities, the friction angle is characteristic of the material itself and is called the basic friction angle. The residual friction angle is slightly lower than the basic friction angle but in many cases, both values are interchangeable. Such values are significantly lower than the so-called peaks friction angle which takes into account the effect of the roughness due to the geometry of the surface of contact between the two parts of a natural rock fracture.

SUMMARY OF THE INVENTION

It is the object of the present invention to provide an apparatus for measuring the friction angle directly from an actual surface, such as a rock surface, on site, without having to remove a rock sample from a rock mass or without having to do any preliminary operation on the surface. The apparatus can be applied against any kind of surface material in any orientation or dip. It is designed to be handheld and used as a daily tool by a rock mechanics engineer or technician.

The apparatus in accordance with the present invention comprises a housing adapted to be held against a surface to be tested, a base which can slide along the inside wall of such housing, a wheel mounted on the lower part of such body and adapted to contact the surface to be tested, means for applying a load on the base to force the wheel against the surface to be tested, means for applying a torque to the wheel and for measuring the maximum torque required to spin the wheel on the surface to be tested at various loads applied to the base.

The means for applying a load on the base preferably comprises a spring mounted on the face of the base opposite the wheel, a wedge assembly mounted in the housing in contact with the upper part of the spring, and a contact knob for applying a variable displacement to a movable component of such wedge assembly to force the wheel against the surface to be tested.

The means for applying and measuring the torque applied to the wheel is preferably a torque gauge. The user of the apparatus notes down on a pad the torque reading corresponding to a given normal load applied to the wheel for the calculation of the friction angle.

The calculated value represents the basic friction angle since the contact area of the wheel with the surface is restricted. The effect of micro-roughness is thus limited and many tests can be performed on the surface in a very short period of time. It allows the user to apply the test on multiple joint surfaces of rock material and to characterize each joint set identified in a specific area to be classified. The apparatus is compact, light, rugged, inexpensive and gives the user a great deal of flexibility.

BRIEF DESCRIPTION OF THE DRAWING

The invention will now be disclosed, by way of example, with reference to the accompanying drawing which illustrates a cross-section of a preferred embodiment of the apparatus.

DETAILED DESCRIPTION OF THE INVENTION

The apparatus comprises a base 10 which can slide along the internal face of a housing in the shape of a cylindrical body 12. A wheel 14 is mounted on a shaft 16 which is rotatably mounted in ball bearings 18 which are secured to the base by screwed supports 20. A spring 22 is mounted at the centre of a cavity 24 in the base. The upper part of the spring is mounted at the centre of a piston 26 which is slidably mounted inside the upper end of the housing Pressure is applied on the spring by means of a wedge assembly which is mounted within a cap 28 screwed on the upper part of the housing. The wedge assembly comprises a lower wedge portion 30 fixed to piston 26 and an upper wedge portion 32 which is slidally mounted on the lower wedge by means of a rotary knob 34. The inside parts of the apparatus are protected from dust and water by rubber seals (not shown) located at the bottom of the base and at the junction of the cylindrical body and the screwed cap.

The axis of the shaft 16 is mounted on a universal shaft 36 which is coming out of the cylindrical body 12 through a slot 38 allowing the universal joint to follow up the movement of the base. When the wheel 14 touches a surface 40 to be tested, a torque gauge 42 may be connected to the universal joint to spin the wheel on the surface and record the maximum torque required to start spinning the wheel.

There are three pods 44 located at the bottom of the cylindrical body at 120 degrees from each other. Those pods are used to avoid contact of the base with the surface 40 in order that only the wheel can touch the surface at any time.

The wheel 14 can be made of material of different hardness and is also removable from its shaft so as to be able to interchange them. To remove the wheel, supports 20 are unscrewed and the wheel with its shaft is removed from the base. The wheel may be removed from the shaft by loosening a screw 46 at the end of the shaft which will free holding plates 48 which are provided to lock the wheel on the shaft.

During use, the above disclosed apparatus is handheld against the surface to be tested with a sufficient pressure to maintain the pods 44 of the cylindrical body 12 and the wheel 14 in good contact with the surface. By turning the knob 34 to a specific value on a scale 50 provided on the cylindrical body, a specific load is applied on the spring which is transmitted to the wheel 14. Since the wheel already touches the surface 40 to be tested, it cannot move. The spring is thus compressed and as it has a constant stiffness, it applies a specific load on the base. This load is transmitted to the wheel. The torque gauge is used to measure the torque required to start spinning of the wheel at the specific load applied on the scale of the knob 34. The torque gauge may be calibrated to read the shear force directly or the torque value may be recorded and divided by the radius of the wheel to provide the shear force. The above values may be used for the calculation of the friction angle using the formula given at the beginning of the specification.

Although the invention has been disclosed with reference to a preferred embodiment, it is to be understood that other alternatives are also envisaged within the scope of the following claims.

We claim:

1. An apparatus for measuring the basic friction angle of a surface of given material comprising:
   a) a housing adapted to be held against a surface of material to be tested;
   b) a base which can slide along the inside wall of said housing;
   c) a wheel mounted on the lower part of said base and adapted to contact the surface to be tested;
   d) means for applying a load on said base comprising a spring mounted on the face of the base opposite to the wheel, a wedge assembly mounted in said housing and adapted to contact the upper part of said spring, and a control knob for applying a variable displacement on a movable component of said wedge assembly to force said wheel against the surface to be tested; and
   e) means for applying a torque to said wheel, and for measuring the maximum torque required to spin the wheel on the surface to be tested at various loads applied to the base.

2. An apparatus as defined in claim 1, wherein said means for applying a torque to said wheel is a torque gauge.

* * * * *